US012800585B2

(12) United States Patent
Joyce

(10) Patent No.: US 12,800,585 B2
(45) Date of Patent: Nov. 17, 2026

(54) SYSTEMS AND METHODS FOR AN INTEGRATED CONSUMABLE FOR ANALYTE TESTING, INCLUDING A PREMIX APPARATUS

(71) Applicant: POLYMER TECHNOLOGY SYSTEMS, INC., Whitestown, IN (US)

(72) Inventor: Joseph P. Joyce, Lafayette, IN (US)

(73) Assignee: POLYMER TECHNOLOGY SYSTEMS, INC., Whitestown, IN (US)

( * ) Notice: Subject to any disclaimer, the term of this patent is extended or adjusted under 35 U.S.C. 154(b) by 351 days.

(21) Appl. No.: 17/812,663

(22) Filed: Jul. 14, 2022

(65) Prior Publication Data

US 2022/0373549 A1 Nov. 24, 2022

Related U.S. Application Data

(62) Division of application No. 16/701,056, filed on Dec. 2, 2019, now Pat. No. 12,146,882.

(60) Provisional application No. 62/774,295, filed on Dec. 2, 2018.

(51) Int. Cl.

*B01L 3/00* (2006.01)
*G01N 33/487* (2006.01)
*G01N 33/50* (2006.01)
*G01N 33/579* (2006.01)

(52) U.S. Cl.

CPC ........ *G01N 33/579* (2013.01); *B01L 3/50853* (2013.01); *G01N 33/48778* (2013.01); *G01N 33/5094* (2013.01); *B01L 3/508* (2013.01); *B01L 2200/0689* (2013.01); *B01L 2300/044* (2013.01); *B01L 2300/0627* (2013.01); *B01L 2300/0672* (2013.01); *B01L 2400/0406* (2013.01); *B01L 2400/0457* (2013.01)

(58) Field of Classification Search

CPC ............... B01L 3/5085; B01L 3/50853; B01L 2200/026; B01L 2300/043; B01L 2300/044; B01L 2400/0677; B01L 2400/0683

See application file for complete search history.

(56) References Cited

U.S. PATENT DOCUMENTS 6,524,530 B1 2/2003 Igarashi et al.
6,943,035 B1 9/2005 Davies
8,906,310 B2 12/2014 Bonecker
9,327,284 B2 5/2016 Rosman et al.

(Continued)

FOREIGN PATENT DOCUMENTS

CN 1767897 A 5/2006
CN 101002094 A 7/2007

(Continued)

OTHER PUBLICATIONS

Office Action issued on Nov. 29, 2023 in related Chinese patent application No. 201980079502.9 (3 pages).

(Continued)

*Primary Examiner* — Charles Capozzi
*Assistant Examiner* — Dwayne K Handy
(74) *Attorney, Agent, or Firm* — Haynes and Boone, LLP; Robert P. Ziemian

(57) ABSTRACT

A system for processing a sample includes a unitary body. The unitary body including a snap lid, the snap lid having a capillary. The unitary body including a lysing container. The unitary body including a test element and a sliding actuator.

13 Claims, 9 Drawing Sheets

(56) References Cited

U.S. PATENT DOCUMENTS

| | | | | |
|---|---|---|---|---|
| 2003/0195435 | A1 | 10/2003 | Williams | |
| 2004/0161788 | A1 | 8/2004 | Chen et al. | |
| 2004/0184954 | A1* | 9/2004 | Guo | B01L 3/5023 422/400 |
| 2005/0196872 | A1 | 9/2005 | Nguyen et al. | |
| 2005/0226786 | A1 | 10/2005 | Hager et al. | |
| 2008/0081378 | A1 | 4/2008 | Ramel | |
| 2009/0117665 | A1* | 5/2009 | Tung | G01N 33/48714 422/68.1 |
| 2013/0216452 | A1 | 8/2013 | Phan et al. | |
| 2015/0182156 | A1* | 7/2015 | Engbersen | B01L 3/5023 435/7.94 |
| 2016/0108393 | A1 | 4/2016 | Lai | |
| 2017/0087549 | A1 | 3/2017 | Patwardhan | |
| 2017/0152081 | A1 | 6/2017 | Crivelli | |
| 2017/0336305 | A1 | 11/2017 | Pierce et al. | |

FOREIGN PATENT DOCUMENTS

| | | | |
|---|---|---|---|
| WO | WO 95/25948 | A1 | 9/1995 |
| WO | WO 2018109091 | A1 | 6/2018 |

OTHER PUBLICATIONS

International Search Report and Written Opinion dated Mar. 19, 2020 issued in related PCT App. No. PCT/US19/64063 (14 pages).

* cited by examiner

SYSTEMS AND METHODS FOR AN INTEGRATED CONSUMABLE FOR ANALYTE TESTING, INCLUDING A PREMIX APPARATUS

CROSSREFERENCE TO RELATED APPLICATIONS

This application is a divisional of U.S. patent application Ser. No. 16/701,056 filed Dec. 2, 2019 which claims the benefit of U.S. provisional application No. 62/774,295, filed on Dec. 2, 2018, which is hereby incorporated by reference in its entirety.

BACKGROUND

In many scenarios, doctors, consumers, and health professionals desire to test for various analytes. Although lab testing is readily available for users, such testing requires users to send away samples and results will not usually be ready quickly. Therefore, point of care (POC) testing systems are desirable. Some of the biggest factors affecting the sale and use of POC testing systems is the convenience, disposability, and ease of use provided by various systems. Therefore, systems that provide such factors are highly desirable.

BRIEF SUMMARY

In one embodiment, a system for processing a sample includes a unitary body. The unitary boding includes a snap lid, the snap lid having a capillary. The unitary boding includes a container containing a mixing agent for a sample, the container including a bottom seal and a top seal. The unitary boding includes a test element. The unitary boding includes a first puncturing element for puncturing the top seal to allow the capillary to enter into the container. The unitary boding includes second puncturing element for puncturing the bottom seal, the bottom seal located such that when punctured the bottom seal releases contents of the container on to the test element. In one alternative, the snap lid is attached to the unitary body via a hinge, around which the snap lid is rotatable, such that the capillary enters an aperture in the unitary body, and the capillary is the first puncturing element. In another alternative, when the snap lid enters the aperture the snap lid snaps in place and is held in place sealing the capillary in an inner portion of the unitary body. Alternatively, when the snap lid enters the aperture the capillary pierces a top seal of the container. In another alternative, when a sliding actuator is slid, a ramp portion of the sliding actuator forces a bottom seal of the container into the capillary piecing the bottom seal, whereby the capillary is the second puncturing element. Alternatively, when a sliding actuator is slid, the sliding actuator forces a bottom seal of the container into the second puncturing element. In another alternative, the second puncturing element is a protrusion on a portion of the body. Alternatively, the system further includes a pushable protrusion, oriented on an opposite side of the device from where the snap lid interfaces with the unitary body, the pushable protrusion actuatable into the bottom seal, wherein the pushable protrusion is the second puncturing element.

In one embodiment, a method for processing a sample includes providing an integrated consumable test system. The test system includes a unitary body. The unitary boding includes a container containing a mixing agent for a sample, the container including a bottom seal and a top seal. The unitary boding includes a test element. The unitary boding includes a first puncturing element for puncturing the top seal to allow the capillary to enter into the container. The unitary boding includes second puncturing element for puncturing the bottom seal, the bottom seal located such that when punctured the bottom seal releases contents of the container on to the test element. The method further includes capturing a sample in the capillary. The method further includes puncturing the top seal with the first puncturing element. The method further includes mixing the sample and the mixing agent. The method further includes puncturing the bottom seal with the second puncturing element. The method further includes flowing the mixed sample and mixing agent to the test element.

In one embodiment, a system for processing a sample includes a unitary body. The unitary body including a snap lid, the snap lid having a capillary. The unitary body including a lysing container. The unitary body including a test element and a sliding actuator. In one alternative, the snap lid is attached to the unitary body via a hinge, around which the snap lid is rotatable, such that the capillary enters an aperture in the unitary body. In another alternative, when the snap lid enters the aperture the snap lid snaps in place and is held in place sealing the capillary in an inner portion of the unitary body. Alternatively, when the snap lid enters the aperture the capillary pierces a first seal of the lysing container. Optionally, when the sliding actuator is slid, a ramp portion of the sliding actuator forces a second seal of the lysing container into the capillary piecing the second seal. Alternatively, the lysing container includes a lysing solution. In another alternative, the capillary is configured to receive a blood sample and deliver the blood sample to the lysing container when the snap lid enters the aperture and the capillary pierces the first seal. Optionally, a mixture of the blood sample and the lysing solution is delivered to the test element when the second seal is pierced. Alternatively, the test element is an electrochemical test strip. In another alternative, the test element is a composite film sensor. Optionally, the system further includes a meter engaging with the unitary body and electrically communicating with the test element and configured to determine a level of an analyte. Alternatively, the analyte is Hb AIC.

BRIEF DESCRIPTION OF THE DRAWINGS

FIG. 5-B shows a cutaway view of an embodiment of an ICA;

DETAILED DESCRIPTION

Certain terminology is used herein for convenience only and is not to be taken as a limitation on the embodiments of the system and methods for an integrated consumable for analyte testing, including a premix apparatus (ICA). In many embodiments, the device tests for AIC. In previous AIC POC testing systems, a three-piece system was utilized. This system included a (1) a discrete microliter capillary device temporarily captured the blood sample and then transferred it into a discrete disposable (2) lysing fluid container and dispenser. The blood and lysing solution would homogenize and then the lysing fluid container would dispense the contents onto a (3) lateral flow assay sensor. In many embodiments of an ICA, these pieces are modified and combined, such that the resulting ICA performs similar tasks to the three separate pieces and enables an AIC POC device.

In many embodiments, in order to achieve this, all of the functions of the discrete components and other functions needed to be combined into one device. Microfluidics is a commonly referred to design protocol for miniaturization, that allows for highly efficient fluid transfer and combination. On one device, blood capture, metering, transfer, on-strip fluid heating, fluid fill detection, chemistry homogenization, lysing storage, fluid e-gating, electronic chemical analysis has been combined.

Previously the steps were taken with separate disposable components. The material packaging, inventory size, consumer instructions and costs are all reduced significantly by the integration onto one device. Advantages include:

1.) Increased consumer use reliability; less components lead to less process failure
2.) Lower inventory requirements and manufacturing time.
3.) Lower product cost
4.) Lower shipping packaging and transit costs.
5.) Higher levels of chemistry accuracy.

Figure 1:
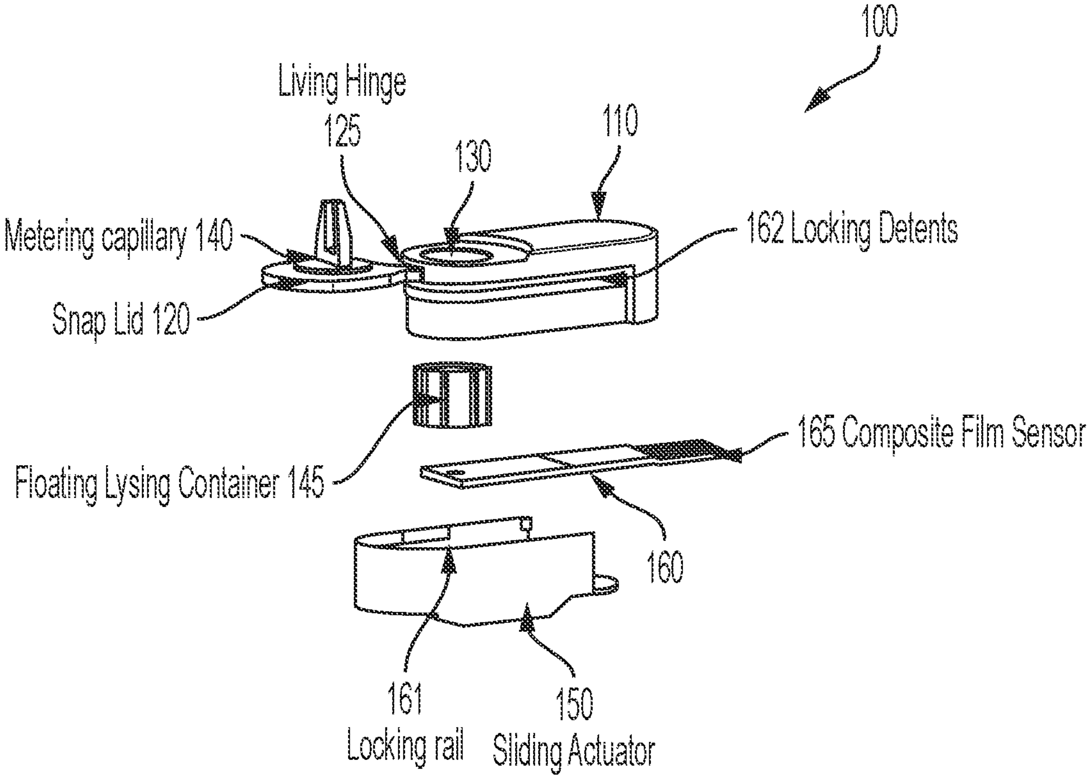
FIG. 1 shows an exploded view of one embodiment of for an integrated consumable for analyte testing, including a premix apparatus (ICA)

FIG. 1 shows an exploded view of one embodiment of an ICA 100. ICA 100 includes a shell portion 110, typical made of plastic or various similar materials (PET, TPE, etc.) Shell portion 110 is attached to snap lid 120 via a living hinge 125. In alternatives, other interconnection hinges/systems may be used other than living hinge 125. In many embodiments, living hinge 125 and snap lid 120, as well as shell portion 110 may be made as a single piece of material. This may be very economical. In most configurations, snap lid 120 must pivot so it can engage aperture 130 in shell portion 110. Snap lid 120 also includes metering capillary 140. Metering capillary is designed to have a capillary portion that will retain a certain volume of blood when touched to blood, such as in the case of finger prick. Various volumes may be configured to be retained in metering capillary 140. In some embodiments, metering capillary 140 may include a sharp tip for lancing, but as show a separate lance is needed to prick a finger or other portion of a user's body. Inside shell portion 110 is a floating lysing container 145 which is moved from a first position to a second position using sliding actuator 150 that interfaces with it and shell portion 110. Composite film sensor 160 is a test strip that tests for the analyte of interest. In many scenarios, this is an electrochemical test strip, however other types of test strips may be used, such as colorimetric and fluorescent, or others. Composite film sensor 160 includes an electrode end 165 (or leads) that may be inserted into a meter and read by a meter. Sliding actuator 150 includes a locking rail 161 that slides to have an interference fitting lock with locking detents 162 in shell portion 110.

Figure 2:
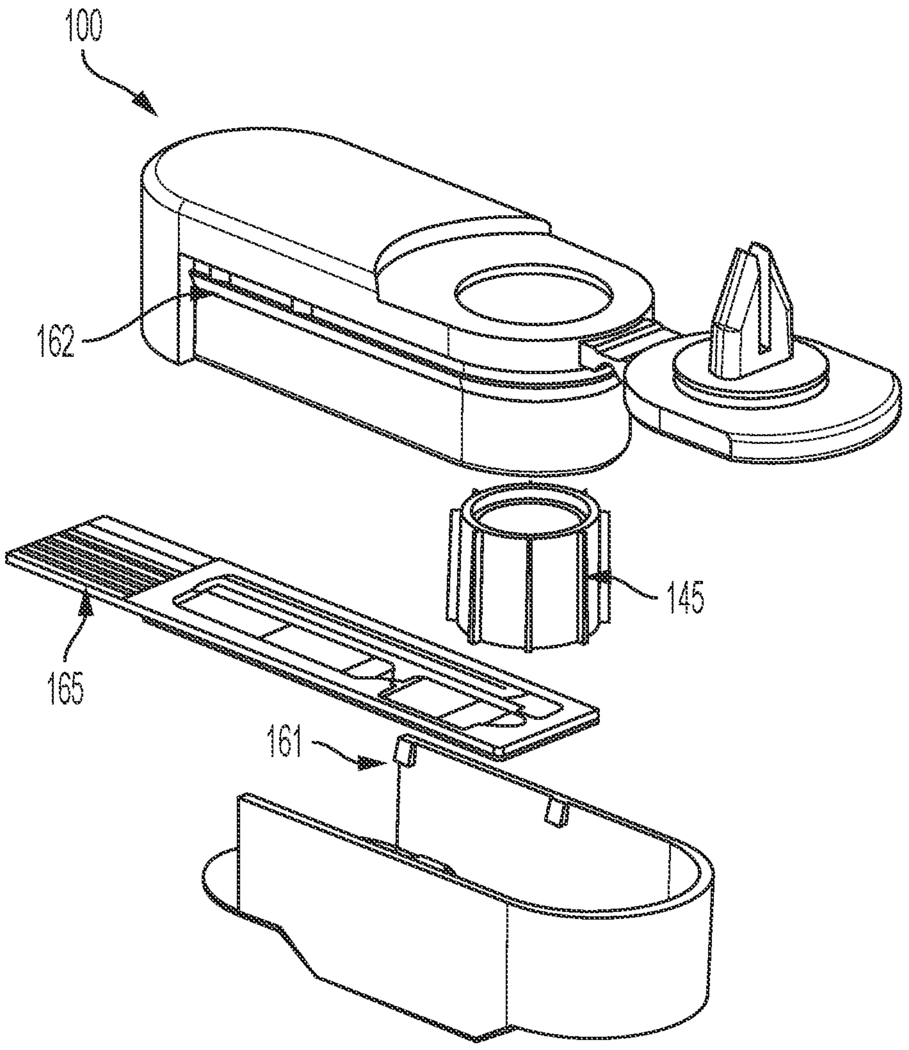
FIG. 2 shows another exploded view of the ICA of FIG. 1.

FIG. 2 shows another exploded view of ICA 100. In this view, locking rail 161 and dents 162 are more clearly visible as are the electrodes 165 of composite film sensor 160.

Figure 3:
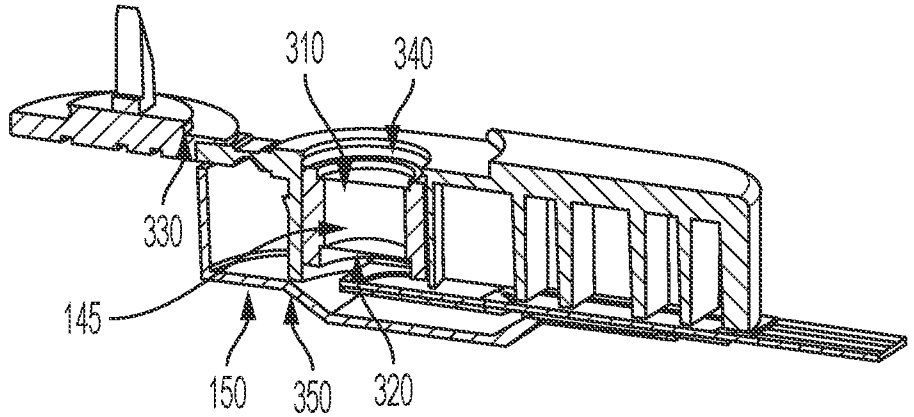
FIG. 3 shows a cut away view of the ICA of FIG. 1 prior to insertion of the snap lid and the sliding of sliding actuator.

FIG. 3 shows a cut away view of ICA 100 prior to insertion of the snap lid 120 and the sliding of sliding actuator 150. In this view, the general set up of the mixing and dosing system is visible. It is important to note that floating lysis container 145 has two seals 310, 320. These are inside of floating lysis container 145 there is a buffer and lysing solution that lyses the red blood cells to release the analyte of interest. In many scenarios, this is hemoglobin A1C. In such a state, the ICA 100 may be used to contact a blood sample and have the metering capillary 140 obtain a sample of the desired size, in many cases 5 microliters. Numerous other volumes are possible based on various possible designs for the ICA 100. Also visible in this view is a groove 330 on snap lid 120 that fits with the protrusion 340 on shell 110 in order to lock snap lid 120 in place when it is rotated 180 degrees about living hinge 125. This cut away view also shows sliding actuator 150 and the ramp 350 of the sliding actuator 150. In many embodiments, instead of a ramp 350, an end arrow piercing protrusion is included. In such scenario, when the sliding actuator 150 is slid, a piercing arrow at the end of the device pierces the bottom side of the floating lysis container, releasing the sample.

Figure 4:
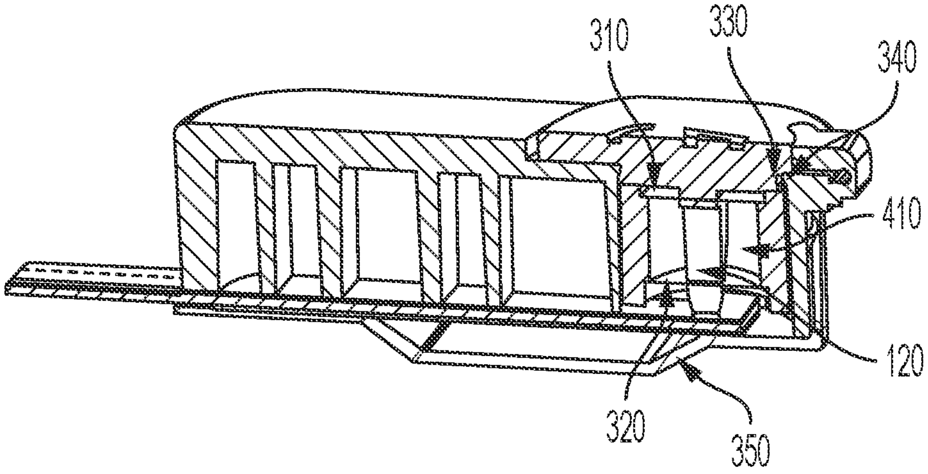
FIG. 4 shows a cut away view of the ICA of FIG. 1 after insertion of the snap lid and the sliding of sliding actuator.
Figure 5A:
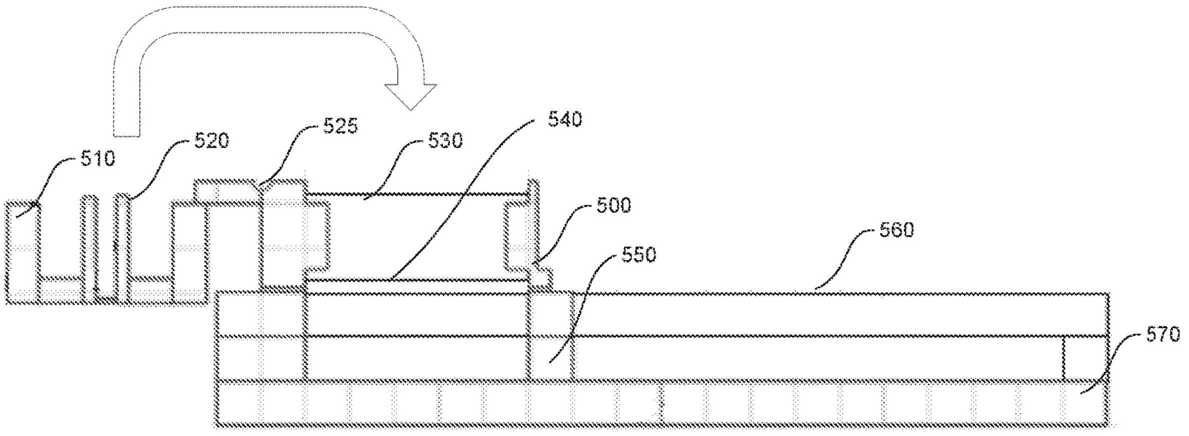
FIG. 5-A shows a cutaway view of an embodiment of an ICA.
Figure 5B:
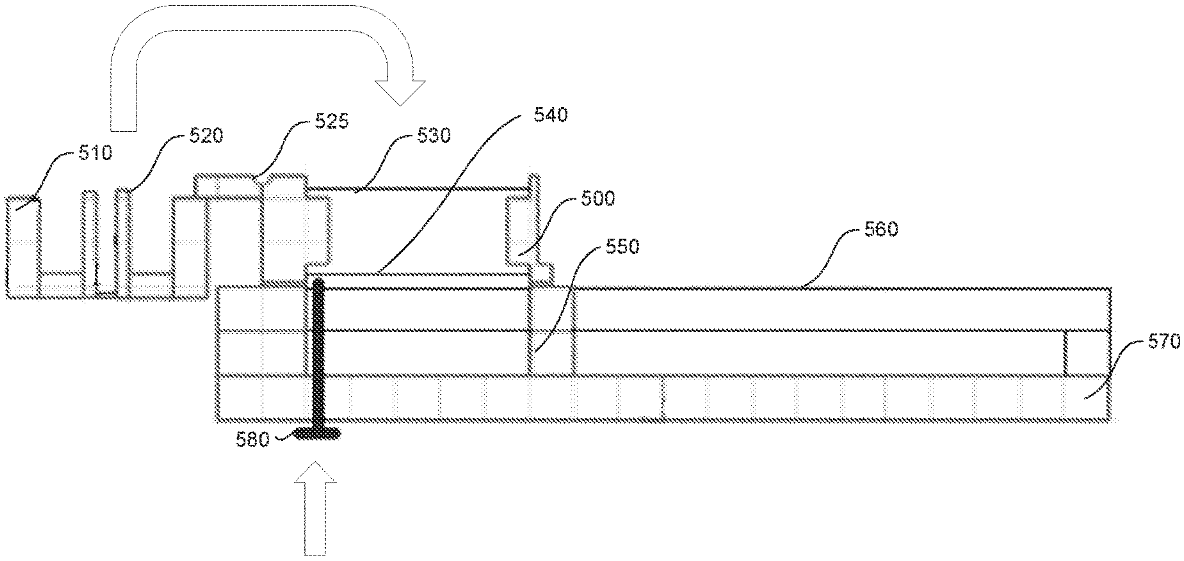

FIG. 4 shows a cut away view of ICA 100 after insertion of the snap lid 120 and the sliding of sliding actuator 150. Here the process becomes clear. After obtaining a sample on metering capillary 140, the snap lid 120 is rotated 180 degrees to penetrate seal 310. At such a time the sample is delivered into lysing area 410 where the lysing mixture is located. The system is mixed, in many scenarios via agitation. Note that at this point seal 320 has not been penetrated, since lysing container 145 may float downwards in the device. However, next ramp 350 is slid into place forcing lysing container 145 upwards toward metering capillary 140 to release the lysed or mixed sample on to composite film sensor 160. Then the sample may flow through various channels and be read by electrodes and an electrical signal may be passed to a meter via the electrode leads 165.

Although the system is described in terms of a lysing solution, various solutions may be located in the floating lysing container. In many embodiments, the system includes a lid that has a protrusion. The protrusion has a capillary area that may receive a sample from a lancet or a supply of bodily fluid. The supply of bodily fluid may be a drop of blood gathering on a finger. The supply of bodily fluid may be from a metered lancet. The protrusion is designed to puncture the floating container (in the other embodiments shown floating lysing container). This may occur via a living hinge or other hinge that connects the cap to the main body of the container. Other methods are possible including a screw on system, whereby a cap is screwed down, causing a protrusion to puncture the floating container. Various mixtures may be included in the floating container, including but not limited to reagents that cause a reaction, reagents that cause a color change, reagents that lyse a sample. Subsequently, the bottom portion of the floating container is punctured. This may be performed via a ramp that slides the module causing the protrusion of the cap to puncture the bottom portion. Alternatively, the device may slide into a puncturing feature or have a protrusion that may be pushed into the floating container from the opposite side.

FIG. SA shows a cut away view of an embodiment of an ICA. ICA 500 includes a cap portion 510 having a protrusion 520 that may receive a sample in its capillary interior and be rotated about hinge 525 to penetrate the seal 530 on the container that is bounded by seal 530 and seal 540. In a second position, protrusion 520 may further penetrate seal 540 and release the sample on to the test strip that is on base 570. The device includes spacers 550 to separate the deal 540 from the test strip. Furthermore, the device includes a shell 560 that seals the interior area of the device. FIG. SB also shows a cutaway view of another embodiment. In this embodiment, instead of advancing the cap portion 510 twice in order to penetrate both seals, a bottom protrusion may be pushed from the other side according to the arrow shown to penetrate the bottom seal 540. In both cases when cap 510 interfaces with the rest of the body via rotation, it forms a seal to prevent fluid leakage. This may be accomplished by a friction fit of snap fit type system and flanges or washers may be included to assist in the seal.

Figure 6:
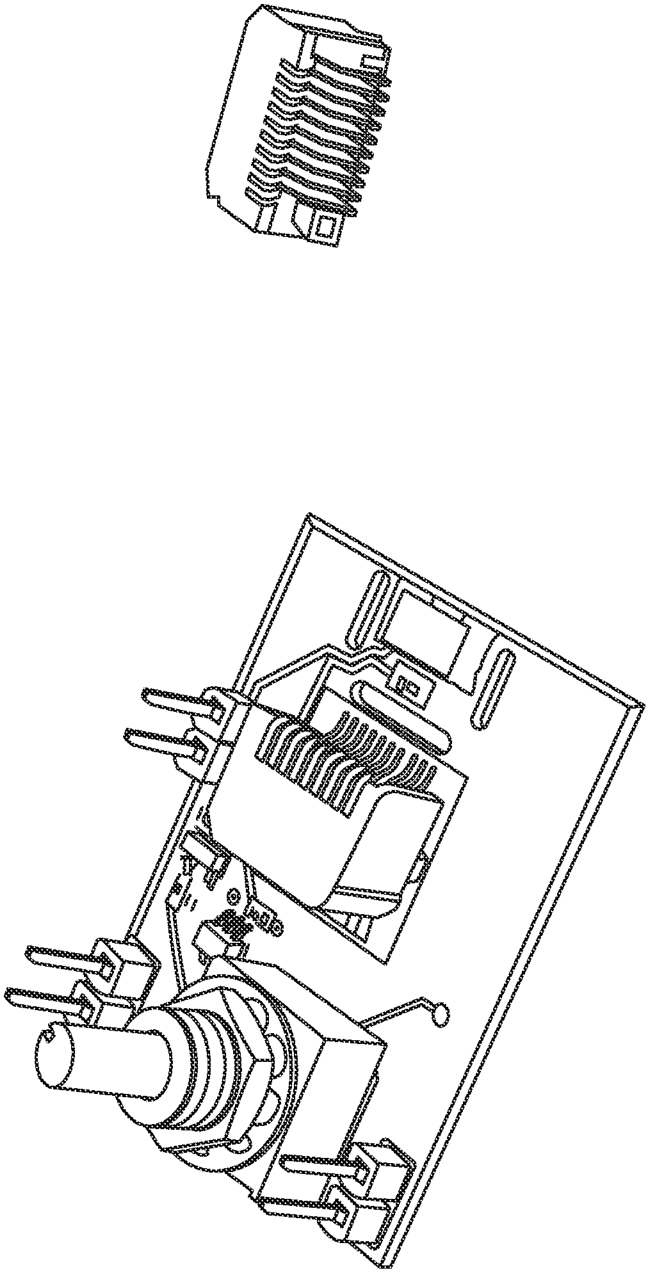
FIG. 6 show an image of a meter that may interface with the electrode ends of a test strip of an ICA.
Figure 7:
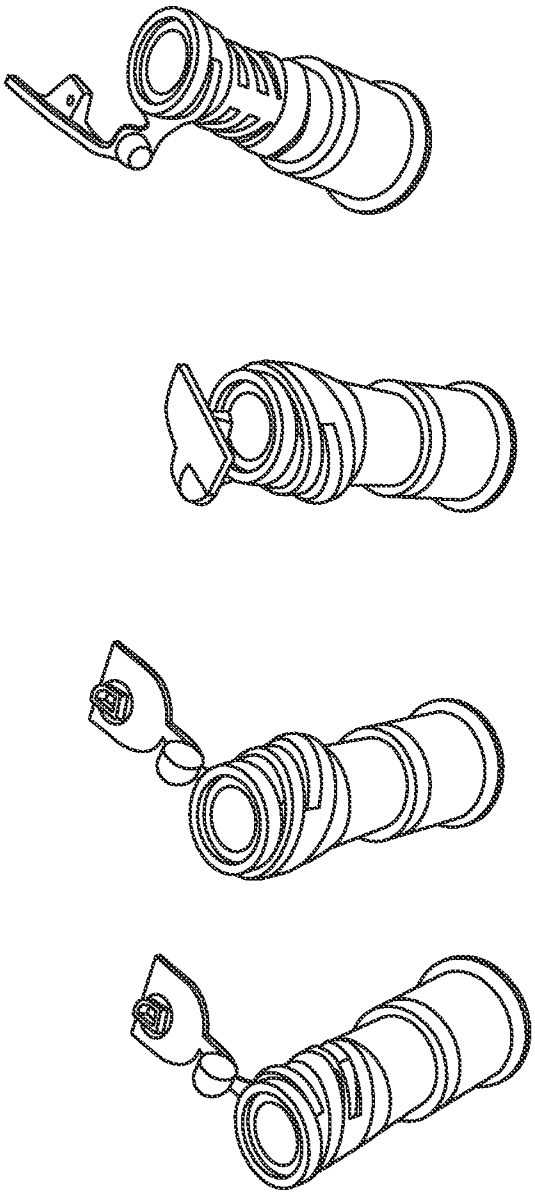
FIG. 7 shows a prototype for a metering capillary and snap lid prior to engaging with the seal of a container holding lysis solution.
Figure 8:
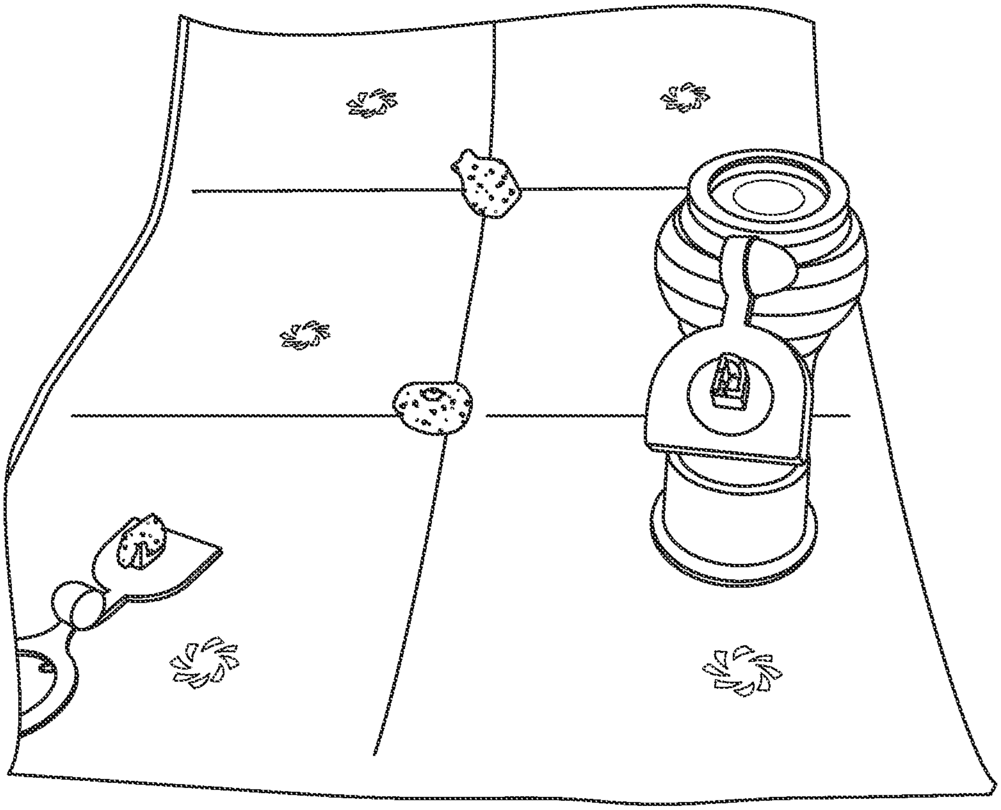
FIG. 8 the prototype for a metering capillary and snap lid prior to engaging with the seal of a container holding lysis solution with a sample on the capillary.
Figure 9:
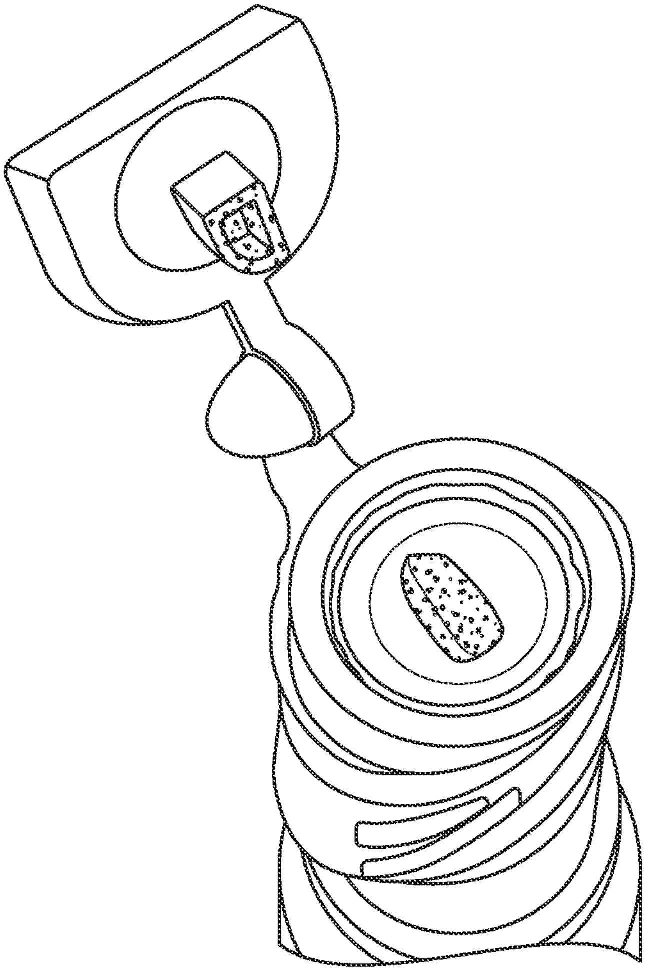
FIG. 9 shows an example of how the capillary can pierce the seal of the container in line with embodiments of the ICA.

FIG. 6 show an image of a meter that may interface with the electrode ends of a test strip of an ICA. FIG. 7 shows a prototype for a metering capillary and snap lid prior to engaging with the seal of a container holding lysis solution. FIG. 7 the prototype for a metering capillary and snap lid prior to engaging with the seal of a container holding lysis solution with a sample on the capillary. FIG. 9 shows an example of how the capillary can pierce the seal of the container in line with embodiments of the ICA.

In many embodiments, the capillary takes a blood sample of a certain size. The metering capillary may be engineered to have a capacity of 5 μl. It has the capability to be altered for other chemistry and other sizes. In many embodiments, the lysis container has the AIC buffer and lysing solution in it. In many embodiments, the sample is applied to the lysing solution by folding over the blood sample dosed, metering capillary so that the living hinged cap rotates 180° piercing the first foil surface in the floating lysing container. Initially pushing down the floating lysing container. The blood sample and lysing solution mix to full homogenous state. Time or agitation acceleration can be used. The actuator is then employed by sliding it to a "closed" state lifting the biosensor strip into a second position causing the tip of the metering capillary to pierce the second foil surface allowing the lysed blood sample solution to be dosed onto the strip's bifurcated assay channels. Then the mixture flows and is part of an electrochemical assay or a antibody/antigens in a sandwich assay or some other type of assay. In many embodiments, it is electrochemical. The consumable is inserted into an analyzer where part of the functional steps are sequenced.

In sum, with respect to the description herein, numerous specific details are provided, such as examples of components and/or methods, to provide a thorough teaching and understanding of embodiments of the present invention. One skilled in the relevant art will recognize, however, that an embodiment can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Similarly, embodiments can be implemented in many forms, and based on the disclosure and teachings provided herein, a person of ordinary skill in the art will appreciate other ways and/or methods to implement an equivalent. Reference throughout this specification to "one embodiment", "an embodiment", or "a specific embodiment" means that a particular feature, structure, or characteristic described in connection with the embodiment is included in at least one embodiment and not necessarily in all embodiments. Thus, respective appearances of the phrases "in one embodiment", "in an embodiment", or "in a specific embodiment" in various places throughout this specification are not necessarily referring to the same embodiment.

Furthermore, the particular features, structures, or characteristics of any specific embodiment may be combined in any suitable manner with one or more other embodiments. It is to be understood that other variations and modifications of the embodiments described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as otherwise operable in certain cases, as is useful in accordance with a particular application.

Additionally, any signal arrows in the drawings/Figures should be considered only as exemplary, and not limiting, unless otherwise specifically noted. Furthermore, the term "or" as used herein is generally intended to mean "and/or" unless otherwise indicated. Combinations of components or steps will also be considered as being noted, where terminology is foreseen as rendering the ability to separate or combine is unclear.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

The foregoing description of illustrated embodiments, including what is described in the Abstract and the Summary and the overview paragraphs, are not intended to be exhaustive or to limit the disclosed system, apparatuses, methods, compositions of matter or other disclosed subject matter to the precise forms disclosed herein. While specific embodiments of, and examples for, the disclosed system, apparatuses, methods, compositions of matter or other disclosed subject matter are described herein for teaching-by-illustration purposes only, various equivalent modifications are possible within the spirit and scope of the disclosed system, apparatuses, methods, compositions of matter or other disclosed subject matter, as those skilled in the relevant art will recognize and appreciate. As indicated, these modifications may be made in light of the foregoing description of illustrated embodiments and are to be included within the true spirit and scope of the disclosure herein provided.

What is claimed as new and desired to be protected by Letters Patent of the United States is:

1. A system for processing a sample, comprising: a unitary body including

- a snap lid, the snap lid having a capillary;
- a floating lysing container, the floating lysing container movable between a first position and a second position within the unitary body;
- a test element;
- a sliding actuator including a ramp portion and a locking rail, the sliding actuator configured to slide in a lateral direction perpendicular to a vertical axis of the floating lysing container along a bottom seal of the floating lysing container, wherein when the sliding actuator is slid in the lateral direction, the ramp portion engages the floating lysing container and forces the floating lysing container from the first position to the second position toward the capillary, and wherein the locking rail slides to have an interference fitting lock with locking detents in the unitary body.

2. The system of claim 1, wherein the snap lid is attached to the unitary body via a hinge, around which the snap lid is rotatable, such that the capillary enters an aperture in the unitary body.

3. The system of claim 2, wherein when the snap lid enters the aperture the snap lid snaps in place and is held in place sealing the capillary in an inner portion of the unitary body.

4. The system of claim 3, wherein when the snap lid enters the aperture the capillary pierces a first seal of the floating lysing container.

5. The system of claim 4, wherein when the sliding actuator is slid, a ramp portion of the sliding actuator forces a second seal of the floating lysing container into the capillary piecing the second seal.

6. The system of claim 5, wherein the floating lysing container includes a lysing solution.

7. The system of claim 6, wherein the capillary is configured to receive a blood sample and deliver the blood sample to the floating lysing container when the snap lid enters the aperture and the capillary pierces the first seal.

8. The system of claim 7, wherein a mixture of the blood sample and the lysing solution is delivered to the test element when the second seal is pierced.

9. The system of claim 8, wherein the test element is an electrochemical test strip.

10. The system of claim 9, wherein the test element is a composite film sensor.

11. The system of claim 10, further comprising a meter engaging with the unitary body and electrically communicating with the test element and configured to determine a level of an analyte.

12. The system of claim 11, wherein the analyte is Hb A1C.

13. A method for processing a sample, comprising:

providing an integrated consumable test system including a unitary body including a snap lid, the snap lid having a capillary;

a floating container containing a mixing agent for a sample, the floating container including a bottom seal and a top seal, the floating container movable between a first position and a second position within the unitary body;

a test element;

a first puncturing element for puncturing the top seal to allow the capillary to enter into the container;

a second puncturing element for puncturing the bottom seal, the bottom seal located such that when punctured the bottom seal releases contents of the floating container on to the test element, the second puncturing element on a sliding actuator having a ramp portion and a locking rail, the sliding actuator configured to slide in a lateral direction perpendicular to a vertical axis of the floating container along the bottom seal of the floating container, wherein when the sliding actuator is slid in the lateral direction, the ramp portion engages the floating container and forces the floating container from the first position to the second position toward the capillary such that the second puncturing element punctures the bottom seal, and wherein the locking rail slides to have an interference fitting lock with locking detents in the unitary body;

capturing a sample in the capillary;

puncturing the top seal with the first puncturing element; mixing the sample and the mixing agent;

puncturing the bottom seal with the second puncturing element; flowing the mixed sample and mixing agent to the test element.

* * * * *